US006482444B1

(12) United States Patent
Bellantone et al.

(10) Patent No.: US 6,482,444 B1
(45) Date of Patent: Nov. 19, 2002

(54) SILVER-CONTAINING, SOL/GEL DERIVED BIOGLASS COMPOSITIONS

(75) Inventors: Maria Bellantone, London; Nichola J. Coleman, Kent; Larry L. Hench, London, all of (GB)

(73) Assignee: Imperial College Innovations, London (GB)

( * ) Notice: Subject to any disclaimer, the term of this patent is extended or adjusted under 35 U.S.C. 154(b) by 0 days.

(21) Appl. No.: 09/593,868

(22) Filed: Jun. 14, 2000

Related U.S. Application Data

(60) Provisional application No. 60/139,014, filed on Jun. 14, 1999.

(51) Int. Cl.$^7$ .......................... A01N 59/16; A61K 33/38
(52) U.S. Cl. ........................................................ 424/618
(58) Field of Search ................................. 424/400, 618

(56) References Cited

U.S. PATENT DOCUMENTS

| | | | |
|---|---|---|---|
| 4,103,002 A | | 7/1978 | Hench et al. |
| 4,272,518 A | | 6/1981 | Moro et al. |
| 4,303,066 A | | 12/1981 | D'Andrea |
| 4,538,603 A | | 9/1985 | Pawelchak et al. |
| 4,539,200 A | | 9/1985 | Quarfoot |
| 4,599,209 A | | 7/1986 | Dautzenberg et al. |
| 4,605,415 A | | 8/1986 | Richez |
| 4,613,502 A | | 9/1986 | Turková et al. |
| 4,788,642 A | | 11/1988 | Suzuki et al. |
| 4,837,285 A | | 6/1989 | Berg et al. |
| 4,851,046 A | | 7/1989 | Low et al. |
| 5,000,746 A | | 3/1991 | Meiss |
| 5,017,627 A | | 5/1991 | Bonfield et al. |
| 5,068,122 A | | 11/1991 | Kokubo et al. |
| 5,126,141 A | | 6/1992 | Henry |
| 5,263,992 A | | 11/1993 | Guire |
| 5,290,544 A | | 3/1994 | Shimono et al. |
| 5,298,260 A | | 3/1994 | Viegas et al. |
| 5,330,770 A | * | 7/1994 | Kuno .......................... 424/618 |
| 5,340,776 A | | 8/1994 | Paschke et al. |
| 5,352,715 A | | 10/1994 | Wallace et al. |
| 5,410,016 A | | 4/1995 | Hubbell et al. |
| 5,470,585 A | * | 11/1995 | Gilchrist ..................... 424/604 |
| 5,501,706 A | | 3/1996 | Arenberg |
| 5,536,614 A | | 7/1996 | Kondo et al. |
| 5,591,453 A | | 1/1997 | Ducheyne et al. |
| 5,648,301 A | | 7/1997 | Ducheyne et al. |
| 5,681,575 A | | 10/1997 | Burrell et al. |
| 5,681,872 A | | 10/1997 | Erbe |
| 5,696,169 A | | 12/1997 | Otsu et al. |
| 5,728,753 A | | 3/1998 | Bonfield et al. |
| 5,753,251 A | | 5/1998 | Burrell et al. |
| 5,766,611 A | | 6/1998 | Shimono et al. |
| 5,807,641 A | | 9/1998 | Oku et al. |
| 5,834,008 A | | 11/1998 | Greenspan et al. |
| 5,840,290 A | | 11/1998 | Hench et al. |
| 5,990,380 A | | 11/1999 | Marotta et al. |
| 6,083,521 A | | 7/2000 | Acemoglu et al. |
| 6,086,374 A | | 7/2000 | Litkowski et al. |

| | | | |
|---|---|---|---|
| 6,228,788 B1 | * | 5/2001 | Jean et al. ..................... 501/32 |

FOREIGN PATENT DOCUMENTS

| | | | |
|---|---|---|---|
| GB | 1418019 | * | 12/1975 |
| JP | 07300339 | * | 11/1995 |
| JP | 08012512 | * | 1/1996 |
| JP | 09301743 | * | 11/1997 |
| WO | 97/17401 | | 3/1994 |
| WO | 98/11853 | | 3/1998 |
| WO | 99/13582 | | 3/1999 |
| WO | 00/66086 | | 11/2000 |

OTHER PUBLICATIONS

Aydin, M., et al, "Deposition Profile of Antibacterial Anodic Silver in Root Canal Systems of Teeth", *J. Biomed. Mater. Res.*, 38(1):59–54, (John Wiley & Sons, Inc.) 1997.

Barrett, E. P., et al., "The Determination of Pore Volume and Area Distributions in Porous Substances. I. Computations from Nitrogen Isotherms", *J. Am. Chem. Soc.*, 73:373–380 (American Chemical Society) 1951.

Bergna, H.E., "The Colloid Chemistry of Silica", *Advances in Chemistry*, Series 234 (American Chemical Society, Washington, DC) 1994.

Bosetti, M., et al., "Effects of Bioactive Glass on Macrophages Activation", *Bioceramics*, 11: 319–322, (Word Scientific Pub. Co.) 1988.

Brinker, C. J., et al., "The Physics and Chemistry of Sol–Gel Processing", *Sol–Gel Science*, 8: 499–503 (Academic Press, Inc.) 1990.

Brinker, C. J., et al., "The Physics and Chemistry of Sol–Gel Processing", *Sol–Gel Science*, 3: 115–119 (Academic Press, Inc.) 1990.

Brunauer, S., et al., "Adsorption of Gases in Multimolecular Layers", *J. Am. Chem. Soc.*, 60: 309–319 (Published Monthly by the American Chemical Society) Feb., 1938.

Carlisle, E. M., "Silicon Biochemistry, Silicon as an Essential Trace Element in Animal Nutrition", *Ciba Foundation Symposium 121,* 123–139 (John Wiley & Sons, New York) 1986.

(List continued on next page.)

*Primary Examiner*—Alton Pryor
(74) *Attorney, Agent, or Firm*—Burns, Doane, Swecker & Mathis, L.L.P.

(57) ABSTRACT

Silver-containing, sol-gel derived bioactive glass compositions and methods of preparation and use thereof are disclosed. The compositions can be in the form of particles, fibers and/or coatings, among other possible forms, and can be used, for example, for treating wounds, improving the success of skin grafts, reducing the inflammatory response and providing anti-bacterial treatments to a patient in need thereof. Anti-bacterial properties can be imparted to implanted materials, such as prosthetic implants, sutures, stents, screws, plates, tubes, and the like, by incorporating the compositions into or onto the implanted materials. The compositions can also be used to prepare devices used for in vitro and ex vivo cell culture.

21 Claims, No Drawings

OTHER PUBLICATIONS

Cartmell, S. H., et al., "Soft Tissue Response to Glycerol–suspended Controlled–release Glass Particulate," *J. Mat. Science: Mat. in Med.,* 9:773–777 (Kluwer Academic Publishers) 1998.

Coleman, J. J., et al., "Mandibular Reconstruction with Composite Microvascular Tissue Transfer", *Medline,* (Abstract) #91023289, 1991.

Freed, J. S., "Use of injectable Biomaterials for the Repair and Augmentation of the Anal Sphincter", *Chemical Abstract,* 119: #195701, 1993.

Fung, M. C. et al., "Silver Products for Medical Indications: Risk–Benefit Assessment", *J. Toxicol.,* 34(1): 119–126 (American Academy of Clinical Toxicology and European Association of Poisons Centres and Clinical Toxicologist) 1996.

Goldman Sachs/U.S. Research, "Advanced Tissue Sciences, (ATS)", (Healthcare: Biotechnology)1–30, 1996.

Greenspan, D. C., et al., "The Evaluation of Degradability of Melt and Sol–Gel Derived Bioglass® In Vitro", *Bioceramics,* 10: 391–394 (Published by Elsevier Science) 1997.

Greenspan, D. C., et al., "Bioactivity and Biodegradability: Melt vs. Sol–Gel Derived Bioglass® In Vitro and In Vivo" *Bioceramics,* 11: 345–348 (World Scientific Publishing Co.) 1998.

Grier, N., "Mercurials—Inorganic and Organic, Chapter 17" and "Silver and its Compounds, Chapter 18", *Disinfection, Sterilization and Preservation* 346–389 (Lea & Febiger, $3^{rd}$ ed.) 1983.

Guo, et al., "Preparation and Studies of Bioactive Glass", *Chemical Abstracts,* v. 120: #144090, 1994.

Hench, L.. L..,, et al., *Biomaterials, An Interfacial Approach,* (Academic Press, New York) 1982.

Hench, L. L., et al., "The Sol–Gel Glass Transformation of Silica", *Phase Transitions, A Multinational Journal,* 24–26: 785–834 (Gordon & Breach Science Publishers, S.A.)1990).

Hench, L. L. et al., "The Sol–Gel Process", *Chemical Reviews* 90: 33–72 (American Chemical Society) 1990.

Hench, L. L., et al., "Biological Applications of Bioactive Glasses", *Life Chem. Rep.,* 13: 187–241 (Harwood Academic Publishers GmbH) 1996.

Hench, L. L., et al., "Introduction to Bioceramics, Chapter 1", *Advanced Series in Bioceramics,* 1: 1–24 (World Scientific) 1993.

Hench, L. L., et al., "Introduction to Bioceramics, Chapter 3", *Advanced Series in Bioceramics,* 3: 41–47, (World Scientific) 1983.

Hench, L. L., et al., "Introduction to Bioceramics, Chapter 4", *Advanced Series in Bioceramics,* 4: 63–79, (World Scientific) 1993.

Hench, L. L., et al., "Introduction to Bioceramics, Chapter 13", *Advanced Series in Bioceramics,* 13: 239–259, (World Scientific) 1993.

Hench, L. L., et al., "Introduction to Bioceramics, Chapter 18", *Advanced Series in Bioceramics,* 18: 319–334, (World Scientific) 1993.

Hench, L. L., et al., "Bonding Mechanisms at the Interface of Ceramic Prosthetic Materials", *J. Biomed. Mater. Res.,* 2 (1)117–141, (John Wiley & Sons, Inc.) 1971 or 2?.

Hench, L. L., et al., "Bioactive Ceramics: Theory and Clinical Applications", *Bioceramics,* 7: 3–14 (Butterworth–Heinemann Ltd.) 1994.

Jansen, B., et al., "In vitro Evaluation of the Antimicrobial Efficacy and Biocompatibility of a Silver–Coated Central Venous Catheter", *J. Biomater. Appl,* 9(1): 55–70 (Technomic Publishing Co.) 1994.

Jansson, G., et al., "Stimulating Effects of Mercuric–and Silver Ions on the Superoxide Anion Production in Human Polymorphonuclear Leukocytes", *Free Rad. Res. Comms.,* 18(2): 87–98 (Harwood Academic Publishers GmbH) 1993.

Kawashita, M., et al., "Preparation of Antibacterial Silver–Containing Silica Glass by Sol–Gel Method," *Bioceramics,* 11: 703–706 (World Scientific Publishing Co.) 1998.

Keeting, P. E.,et al., "Zeolite A Increases Proliferation, Differentiation, and Transforming Growth Factor β Production in Normal Adult Human Osteoblast–Like Cells In Vitro", *J. Bone & Miner. Res.,* 7(11): 1281–1289 (Mary Ann Liebert, Inc.) 1992.

Kelton, P. L., MD, "Skin Grafts", *Selected Readyings in Plastic Surgery,* 7(2): 1–25, (Baylor University Medical Center) 1992.

Kim, T. N., et al., "Antimicrobial Effects of Metal Ions ($A^+$, $Cu^2$, $Zn^{2+}$) in hydroxyapatite", *J. Mater. Sci.–Mat. Med.,* 9: 129–134 (Chapman & Hall) 1998.

Kobuko, T., et al., "Solutions Able to Reproduce in Vivo Surface–structure Changes in Bioactive Glass–Ceramic $A–W^{3}$", *J. Biomed. Mater. Res.,* 24:721–734 (John Wiley & Sons, Inc.) 1990.

Liau, S. Y., et al, "Interaction of Silver Nitrate with Readily Identifiable Groups: Relationship to the Antibacterial Action of Silver Ions", *Lett. Appl. Microb.,* 25: 279–283 (Published for the Society for Applied Bacteriology by Blackwell Science) 1997.

Loeffler, U., et al., "Kit for in Situ Formation of Topical Gel for Enzyme Release in Wounds", *Chemical Abstracts,* 127: 140–572, 1997.

Nogami, M. et al., "Glass Formation Through Hydrolysis of $Si(OC_2H_5)_4$ With $NH_4$ and HCI Solution", *J. Non–Chryst. Solids,* 37: 191–201 (North–Holland Publishing Co) 1980.

Pereira, M. M., et al., "Effect of Texture on the Rate of Hydroxyapatite Formation on Gel–Silica Surface", *J. Am. Chem. Soc.,* 78(9): 2463–2368, (Am. Ceramic Soc.) 1995.

Pereira, M. M., et al., "Homogeneity of Bioactive Sol–Gel Derived Glasses in the System $CaO–P_2O_5–SIO_2$", *J. Mater. Synth. Proces.,* 2(3): 189–196 (Plenum Pub. Co. 1994.

Pereira, M. M., et al., "Mechanisms of Hydroxyapatite Formation on Porous Gel–Silica Substrates", *J. Sol–Gel Sci. Technol,,* 7: 59–68 (Kluwer Academic Pub.)1996.

Pérez–Pariente, J., et al., "Influence of Composition and Surface Characteristics on the in Vitro Bioactivity of $SiO_2–CaO–P_2O_5–MgO$", *J. Biomed. Mater. Res.,* 170–175, (John Wiley & Sons, Inc.) 1999.

Rabinovich, E. M., et al., "Fluorine in Silica Gels", *Better Ceramics Through Chemistry II,* 251–259 (Brinker, Clark, Ulrich, eds, Materials Research Society, Pittsburgh, PA) 1986.

Reese, A. C., et al., "Role of Fibronectin in Wound Healing", *Current Advances in Oral and Maxillofacil Surgery,* 1: 1–25, (no date).

Scalzo, M., et al., "Antimicrobial Activity of Electrochemical Silver Ions in Nonionic Surfactant Solutions in Model Dispersions", *j. Pharm. Pharmacol.,* 48(1): 60–63 (The Royal Pharmaceutical Society of Great Britain) 1996.

Shapiro, L., et al,. "Ciliary Neurotropic Factor Combined with Soluble Receptor Inhibits Synthesis of Proinflammatory Cytokines and Prostaglandin-$E_2$ in Vitro" *Exp. Cell. Res.,,* 215(1): 51–56, (Academic Press, Inc.) 1994.

Shirkanzadeh, M., et al., "Formation of Carbonate Apatite on Calcium Phosphate Coatings Containing Silver Ions," *J. Mat. Science, Mat. in Medicine,* 9: 385–389 (Kluwer Academic Publishers) 1998.

Sing, K. S. W., et al., "Reporting Physisorption Data for Gas/Solid Systems with Special Reference to the Determination of Surface Area and Porosity" *Pure Appl. Chem.,* 57(4): 603–619 (Blackwell Scientific Publications) 1985.

Slawson, R. M., et al., "Germanium and Silver Resistance, Accumulation, and Toxicity in Microorganisms" *Plasmid,* 27(1): 72–79 (Bimonthly by Academic Press, Inc.)1992.

Stoor, P., et al., "Interactions Between the Frontal Sinusitis–Associated Pathogen *Haemophilus Influenza* and the Bioactive Glass S53P4", *Bioceramics,* 8: 253–258 (Pergamon) 1995.

Stoor, P. et al., "Antibacterial Effects of a Bioactive Glass Paste on Oral Microorganisms", *Acta Odontol. Scand.,* 56:161–165 (Scandinavian University Press) 1998.

Theilmann, et al, "Two–Layer Bandage Made of a Polymer and a Water–absorbing Material", *Chemical Abstracts* 112: 240557, 1990.

Thompson, M., et al., *A Handbook of Inductively Coupled Plasma Spectrometry,* (Blackie) 1983.

Ulich, T. R., et al., "Intratracheal Injection of LPS and Cytokines, V. LPS Induces Expression of LIF and LIF Inhibits Acute Inflammation", *Am. J. Physiol.,* 267 (4, pt. 1/2):L442–446 (The Am. Physiological Soc.) 1994.

von Nägeli, C., "Tötliche Wirkung von angeblich reinem Wasser auf lebende Zellen", *Denkschriften der Schweiz Naturforsch. Ges.,* 33:1–10, 1893.

Vrouwenvelder, C. A., et al., "Histological and Biochemical Evaluation of Osteoblasts Cultured on Bioactive Glass, Hydroxylapatite, Titanium Alloy, and Stainless Steel", *J. Biomed. Mater. Res.,* 27: 465–475 (John Wiley & Sons, Inc.) 1993.

Warren, L. D. et al., "An Investigation of Bioglass Powders: Quality Assurance Test Procedure and Test Criteria", *J. Biomed. Mater. Res.,* 23(A2): 201–209 (John Wiley & Sons, Inc.) 1989.

Wells, T. N. C., et al, "Mechanism of Irreversible Inactivation of Phosphomannose Isomerases by Silver Ions and Flamazine", *Biochemistry,* 34(24): 7896–7903 (American Chemical Society) 1995.

Wood, S, "Case Study: Traumatic Pressure Sore of the Left Lateral Malleolus", *Medline,* (Abstract) 9315 543, 1993.

Wright, J. B., et al., "The Comparative Efficacy of Two Antimicrobial Barrier Dressings: In–vitro Examination of Two Controlled Release of Silver Dressings," *Wounds: A Compendium of clinical Research and Practice,* 10(6): 179–188, (Westaim Biomedical Corp.)1998.

Zhong, J., et al., "Porous Sol–Gel Bioglass® From Near–Equilibrium Drying", *Bioceramics,* 10, 265–268 (Elsevier Science) 1997.

* cited by examiner

SILVER-CONTAINING, SOL/GEL DERIVED BIOGLASS COMPOSITIONS

The present invention relates to silver-containing sol-gel bioglass compositions and methods of preparation and use thereof, for example, in preparing biodegradable sutures, bone graft substitutes, matrices for use in tissue engineering applications. This application claims priority to U.S. Ser. No. 60/139,014, filed Jun. 14, 1999, the contents of which are hereby incorporated by reference.

FIELD OF THE INVENTION

BACKGROUND OF THE INVENTION

Materials used for implantation in the human body to replace damaged or diseased tissue must be biocompatible and mechanically suitable for their intended use. Metallic and polymeric materials for biomedical applications present many problems due to their high Young's modulus (compared with that of bone), the formation of a non-adherent fibrous capsule (the resulting movement of which can lead to deterioration in function of the implant), or sometimes to their degradation products.

There is an increasing clinical use of bioactive glass and glass-ceramics because they offer the possibility of improving the long-term survivability of prostheses and improved repair of aged, diseased or damaged bone. These materials tend to form mechanically strong bonds to bone by means of a series of chemical reactions at the bone-implant interface. One of the major advantages of using a bioactive glass is the ability to control the surface chemistry, and in doing so, exerting control over the rate of bonding to the tissue.

Many biocompatible and bioactive biomaterials have been implanted. Associated problems of infections due to the intrinsic nature of an illness and to surgical intervention can arise as a consequence of implantation, even with currently aseptic surgical procedures.

Bioglass® is one example of a biocompatible material used to prepare implants. Bioglass® is often used to repair damage caused in bones, teeth, and skin where the potential for bacterial or mycotic infections is always present. An important example is osteomyelitis, one of the most dangerous diseases which is caused, in the majority of cases, by S. aureus, Salmonella or K. kingea (in children).

Even in cases of non-infectious diseases, post-operative conditions often require antibiotic treatment, which is usually administered orally. Unfortunately, this can cause bacteriological resistance to the drug, and often depletes the benign microbial flora normally present in the body, leading to gastrointestinal side effects.

Recent efforts have been focused on developing modified implant materials with antibacterial properties. Such implant materials must have suitable mechanical and chemical properties for their intended use. It would be advantageous to provide additional implant materials with antibacterial properties. The present invention provides such materials.

SUMMARY OF THE INVENTION

Silver-containing sol-gel derived bioactive glass compositions and methods of preparation and use thereof are disclosed. The compositions can be in the form of fibers, which can have any diameter between 1 $\mu$ and 150 $\mu$m and can be either continuous or discontinuous or particles which can have any diameter for example, from 0.5 $\mu$m to 3 mm, or coatings which can have thicknesses, for example, from 0.05 to 100 $\mu$m. The bioactive glass (bioglass) used in the compositions includes various salts in the following ranges (weight percent of the bioglass composition):

| | |
|---|---|
| $SiO_2$ | 40–90% |
| CaO | 6–50% |
| $P_2O_5$ | 0–12% |
| $Ag_2O$ | 0.1–12% |

The fibers can be woven into mats and used to make structures useful, for example as bone graft substitutes and coverings for bony defects. The fibers can also be used to make three dimensional structures for preforms to be impregnated with polymers, for example biodegradable polymers. Such structures can be linked, covalently or ionically, to bioactive compounds, for example growth factors, antibiotics, antivirals, nutrients and the like, to enhance tissue repair and promote healing.

The compositions, preferably in the form of fibers or particles, can be incorporated into implanted materials such as prosthetic implants, sutures, stents, screws, plates, tubes, and the like. The compositions in the form of particles can be applied as bioactive layers on prosthetic implants. The compositions in the form of bioactive sol-gel coatings can be applied on the surface or in the pores of prosthetic implants of various configurations.

The compositions are also useful for tissue engineering applications. An advantage of using these compositions is that anti-bacterial properties can also be imparted to devices used for in vitro and ex vivo cell culture when the compositions are incorporated into tissue engineering devices.

DETAILED DESCRIPTION OF THE PREFERRED EMBODIMENTS

Silver-containing sol-gel derived bioactive glass compositions and methods of preparation and use thereof are disclosed. The compositions can be in the form of fibers, which can have any diameter between 1 $\mu$ and 150 $\mu$m and can be either continuous or discontinuous, particles which can have any diameter, for example from 0.5 $\mu$m to 3 mm, or coatings which can have thicknesses, for example from 0.05 to 100 $\mu$m. The compositions are prepared using a sol-gel method and can be used for a variety of medical uses, for example bone repair, biodegradable sutures, and tissue engineering applications.

I. Composition

As used herein the terms "bioactive glass" or "biologically active glass" mean an inorganic glass material having an oxide of silicon as its major component and which is capable of bonding with growing tissue when reacted with physiological fluids.

Bioactive glasses are well known to those skilled in the art, and are disclosed, for example, in *An Introduction to Bioceramics*, L. Hench and J. Wilson, eds. World Scientific, New Jersey (1993), the contents of which are hereby incorporated by reference.

The glass preferably includes between 40 and 90% by weight of silicon dioxide ($SiO_2$), between about 6 and 50% by weight calcium oxide (CaO), between about 0 and 12% by weight phosphorus oxide ($P_2O_5$) and between about 0.1 and 12% by weight silver oxide ($Ag_2O$). More preferably, the glass includes between 45 and 86% by weight of silicon dioxide oxide ($SiO_2$), between about 10 and 36% by weight calcium oxide (CaO), between about 3 and 12% by weight phosphorus oxide ($P_2O_5$) and between about 3 and 12% by weight silver oxide ($Ag_2O$).

$CaF_2$, $B_2O_3$, $Al_2O_3$, MgO and $K_2O$, $Na_2O$ may be included in the composition in addition to silicon, sodium, phosphorus and calcium oxides. Other silver salts than silver oxide can optionally be used. The preferred range for $B_2O_3$ is between 0 and 10% by weight. The preferred range for $K_2O$ is between 0 and 8% by weight. The preferred range for $Na_2O$ is between 0 and 20% by weight. The preferred range for MgO is between 0 and 5% by weight. The preferred range for $Al_2O_3$ is between 0 and 3% by weight.

It is preferred to use reagent grade glass, especially since the glass is used to prepare materials which ultimately may be administered to a patient.

In a preferred embodiment, the silver-containing, sol-gel derived bioactive glass is formed from various salts in the following ranges (weight percent of the bioglass composition):

| | |
|---|---|
| $SiO_2$ | 45–86% |
| CaO | 10–36% |
| $P_2O_5$ | 3–12% |
| $Ag_2O$ | 3–12% |

Examples of preferred sol-gel derived bioactive glasses are shown below in Table 1, any of which can be modified to include an effective, anti-bacterial amount of silver ions using the methods described herein.

TABLE 1

| Composition (mol. %) of bioactive gel-glasses. | | | |
|---|---|---|---|
| Designation | $SiO_2$ | CaO | $P_2O_5$ |
| 49S | 50 | 46 | 4 |
| 54S | 55 | 41 | 4 |
| 58S | 60 | 36 | 4 |
| 63S | 65 | 31 | 4 |
| 68S | 70 | 26- | 4 |
| 72S | 75 | 21 | 4 |
| 77S | 80 | 16 | 4 |
| 86S | 90 | 6 | 4 |

Higher CaO contents provide larger pore volumes and the onset of hydroxycarbonate apatite (HCA) deposition is accelerated. Gel-glasses with higher $SiO_2$ contents tend to have larger surface areas and exhibit higher growth rates of formation of an HCA layer.

Silver Salts

Any suitable silver salt can be used which can be incorporated into the bioactive glasses using a sol-gel method. Silver oxide is a preferred salt. Other suitable salts include silver nitrate, silver acetate, silver bromide and silver chloride. The amount of silver in the compositions is generally in the range of between about 0.1 and 12 percent by weight, preferably between about 3 and 12 percent by weight.

The toxicity limit for the ingestion of soluble silver salts is about 1 gram for humans, but it is not generally considered a threat to life, as an accidental exposure to high doses of silver is extremely rare. Indiscriminate use of silver-containing pharmaceutical preparations and devices can lead to toxic reactions such as argyria. The term "effective, antibacterial amount" of silver refers to an amount effective to significantly reduce the amount of bacteria in an area proximate to where the bioactive glass is present. This amount would be expected to vary depending on a variety of factors, including the type of bacteria, the bacterial concentration, the type of media and the intended use. Those of skill in the art can readily determine an appropriate, antibacterial amount of silver to use. The bioactive glass compositions can be adjusted to include a variety of concentrations of silver ions.

The antimicrobial action of silver has been verified on a number of gram positive and gram negative bacteria, and fungi, among which are *E. coli, P. aeruginosa, S. epidermis, C albicans*. The enzymes on which the inactivating influence has been studied include; urocinase, β-galactosidase, phosphomannose-isomerase, and several oxygenases. It has been postulated that silver exerts its toxicity at multiple sites, among which are the respiratory chain, the phosphate uptake and storage, and the cell wall synthesis. The overall result of these alterations is a lethal leakage of metabolites from the cell, including phosphate and potassium ($K^+$).

The mechanism of action of $Ag^+$ is believed to be related to its complexation to membranes, enzymes and other cellular components. The silver ion is strongly chelated by electron donor groups such as amines, hydroxyls, phosphate and thiols. The latter are thought to be the most important chelating groups, according to microbiological, biochemical and electrochemical data. The silver ion is believed to interact with protein molecules via exposed cysteine residues.

II. Methods for Preparing the Fibers, Particles and Coatings

Sol-Gel Method

The compositions are prepared using a sol-gel method. When compared with conventional glass production techniques, there are a number of advantages associated with the sol-gel process: lower processing temperatures, purer and more homogenous materials, good control over the final composition, and tailoring of the surface and pore characteristics of the product.

Alkoxide derived gel-glasses of the system $SiO_2$—CaO—$P_2O_5$ present an expanded compositional range of bioactivity over bioactive glasses made by melt processes. The difference in bioactive behavior relates directly to the structure of sol-gel derived materials. The gel-glasses have a much higher surface area, a higher concentration of silanol groups per unit area on the surface and a higher concentration of metastable three and four membered siloxane rings. The bioactivity is influenced by the texture of the material as well as the chemical composition.

The gel-glasses are ideally suited as bone graft materials, due to their higher resorption rates in vitro and in vivo. Furthermore, the rate of soluble silicon species released during HCA formation, and the stimulation of bone growth are improved compared with those of the melt-derived bioactive glass.

The compositions can be prepared, for example, by synthesizing an inorganic network by mixing metal alkoxides in solution, followed by hydrolysis, gelation, and firing to produce a porous matrix or a dense glass. The firing can be done at relatively high temperatures (600–1100° C.), and can also be done at low temperatures (on the order of about 200 to 250° C.). The sol-gel process used herein uses a four or more component system, including at least $SiO_2$, CaO, $P_2O_5$ and a silver salt, for example, $Ag_2O$. In one embodiment, the silver-containing sol-gel bioactive glass is produced as a gel network from tetraethoxysilane (TEOS), phosphorous alkoxide, calcium nitrate and silver oxide in water-ethanol solution.

The process, and the types of reactions which typically occur in sol-gel formation, is described in more detail below.

Aqueous Solutions of $SiO_2$

The first step of the sol-gel process typically involves mixing the precursor, silicon alkoxide, solvent (generally water), and an acid or alkaline catalyst. This step can dramatically affect the homogeneity of a multi-component gel, which is also influenced by the nature and reactivity of the precursors, the nature and solubility of the reactants in the selected solvent, the concentration of the selected solvent, the sequence of addition, the pH and the time and temperature of the reaction.

After mixing, the alkoxide precursor is hydrolyzed to silicic acid, which then condenses to yield the silica gel. The hydrolysis reactions are shown below, where R is an alkyl group:

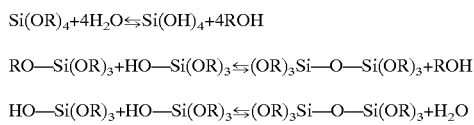

$Si(OR)_4 + 4H_2O \leftrightharpoons Si(OH)_4 + 4ROH$ $RO—Si(OR)_3 + HO—Si(OR)_3 \leftrightharpoons (OR)_3Si—O—Si(OR)_3 + ROH$ $HO—Si(OR)_3 + HO—Si(OR)_3 \leftrightharpoons (OR)_3Si—O—Si(OR)_3 + H_2O$ Hydrolysis is believed to occur via bimolecular nucleophilic attack ($S_N2$) of water on the Si atom, and can be catalyzed by acids or bases. The nature of the alkoxide group (R) influences the rate of hydrolysis through inductive and steric effects. When R is an electron-withdrawing group it accelerates the reaction, and if the R group is bulky it slows down the reaction rate.

When producing a multi-component system, TEOS, rather than tetramethoxysilane (TMOS) (which only takes minutes to hydrolyze), is the chosen precursor in order to have better control on the rate of hydrolysis. Tetraethoxyphosphate (TEP) is used as a convenient source of phosphate monomers. Soluble metal salts, like nitrates, can also be used to introduce modifier atoms. The condensation is catalyzed by the same catalysts used in the hydrolysis and its reaction rate changes with the pH value of the solution.

The pH conditions also affect how coarse and consolidated the resulting gel will be. The shape and the size of polymeric structural units are determined by the relative values of the rate constants for hydrolysis and polycondensation reactions. Fast hydrolysis and slow condensation favor formation of linear polymers; on the other hand, slow hydrolysis and fast polymerization results in larger, bulkier polymers.

As the sol particles grow and collide condensation occurs and macroparticles form. The sol becomes a gel when it can support a stress elastically.

Aging

The aging step involves maintaining the cast object for a period of time (typically from hours to days) immersed in liquid. During aging, polycondensation continues along with localized dissolution and re-precipitation, until free reactive species and reactive sites have all reacted. This process, that decreases the porosity and strengthens the gel, is called syneresis; it causes the gel to shrink and expel the pore liquors.

Along with syneresis, another phenomenon, called Ostwald ripening, takes place. This is an irreversible process involving preferential dissolution of high potential energy convex surfaces, followed by deposition on low energy concave surfaces. Thus, necks begin to form between primary particles and smaller pores are filled at the expense of the bigger ones. This coarsening process is usually slower compared with the syneresis, but it can affect the texture of the gel, particularly when the aging takes place at high temperatures or high pH values.

Drying

During drying, the liquid is removed from the interconnected pore network. Strong capillary stresses can develop and cause the gel to crack unless the drying process is controlled by decreasing the solid-liquid interfacial tension. This can be achieved in a number of ways: by addition of surfactants; by hypercritical evaporation which eliminates the solid-liquid interface; or by obtaining monodisperse pore sizes from controlling the rates of hydrolysis and condensation.

Stabilization and Densification

Removal of the surface silanol groups results in a chemically stable porous material. This can be achieved using thermal and/or chemical methods. Chemical methods often involve modification of the silica surface by replacing the silanol groups with more hydrophobic and less reactive species (e.g., chlorides and fluorides). Heating above 400° C. results in an irreversible dehydration due to the increasing elimination of isolated silanol groups and to the structural relaxation which takes place.

In multi-component systems the calcination process also serves to degrade other species that are present in the gel (e.g., calcium nitrate, $Ca(NO_3)_2$). Nitrate species are undesirable in bioapplications, and are also a source of in-homogeneity. They also remain in the specimen after drying and must be decomposed. Note that the decomposition of pure $Ca(NO_3)_2$ occurs at 561° C. Hence this temperature must be exceeded during successful stabilization if such groups are present.

Heating at temperatures between 800° C. and 1500° C. (depending on the initial porosity, interconnectivity, atmosphere, and composition) will densify the gel to become a consolidated glass with a density substantially equivalent to that of glasses made by conventional melting and casting.

Adjusting the Pore Volume of the Compositions

Suitable pore diameters are between 20 and 400 Å. Pore diameters larger than 0.1 microns can be achieved using a sintering and/or foaming processes. The sintered structure may then be impregnated with a variety of materials, as discussed in more detail below.

To aid in preparing glass compositions with high porosity, the glass composition can include a material which can be preferably leached out of the glass composition, and, in doing so, provide the composition with high porosity. For example, minute particles of a material capable of being dissolved in a suitable solvent, acid, or base can be mixed with or incorporated into the glass, and subsequently leached out. The resulting voids have roughly the same size as the particle that was leached out. The size of the pores and degree of porosity also depends on the amount of added material relative to the amount of glass. For example, if the leached material constituted about 80% of the glass, then the glass would be approximately 80% porous when the material was leached out. When leaching the glass composition, care should be taken not to leach out a significant amount of those components which add to the bioactivity of the glass, i.e., the calcium and phosphorus oxides, or the antibacterial properties of the glass, i.e., the silver ions.

Preparation of Bioactive Glass Fibers

Continuous fibers can be prepared, for example, by extruding the sol through a spinneret. The fibers can then be aged, dried, and thermally stabilized. Long fibers may be woven into a mesh, short fibers may be combined by mixing them with a degradable adhesive, such as a solution of carboxymethylcellulose (CMC). The resulting material is then heated in a kiln to sinter the material and burn off the binder.

Preparation of Bioactive Glass Coatings

Coatings can be prepared using means well known to those of skill in the art, including dipping an article to be coated into an appropriate sol-gel solution which is then treated to form the sol gel, and spraying the article to be coated with particles of the bioactive glass.

B. Methods of Shaping the Fiber into Desired Structures

After the composition has been spun into a fiber, for example in a spinneret, the resulting fiber can be shaped into desired structures. In one embodiment, the fiber is merely wound and can be used as a degradable suture material. In other embodiments, the fiber is mixed with various additional components, including polymeric materials, and shaped into desired articles of manufacture. The shaping can be performed via any acceptable means, including laser ablation, extrusion, molding techniques, and the like.

The fibers can be formed into a mesh or fabric (woven or non-woven). The mesh can be used, for example, in wound healing and wound covering. In one embodiment, the fibers are woven into mats or other structures. The resulting material can be used to make structures useful, for example as bone graft substitutes and coverings for bony defects.

The fibers can also be used to make three dimensional structures for preforms to be impregnated with polymers, for example biodegradable polymers. Such structures can be linked, covalently or ionically, to bioactive compounds, for example, growth factors, antibiotics, antivirals, nutrients and the like to enhance tissue repair and promote healing.

The fibers can be incorporated into implanted materials, such as prosthetic implants, sutures, stents, screws, plates, tubes, and the like.

The fibers (as well as particles) are also useful for tissue engineering applications. An advantage of using these fibers is that anti-bacterial properties can also be imparted to devices used for in vitro and ex vivo cell culture when the fibers are incorporated into tissue engineering devices.

When the fiber has a relatively high porosity, it has a relatively fast degradation rate and high surface area, in comparison to non-porous bioactive glass fiber compositions. The degree of porosity of the glass is between about 0 and 85%, preferably between about 10 and 80%, and more preferably, between about 30 and 60%.

II. Formulations Including Bioactive Glass

The form of the bioactive glass (particles, fibers, and the like) depends in large part on the intended use of the compositions. Those of skill in the art can readily select an appropriate form for the bioactive glass for an intended use. Examples of applications of the silver-containing sol-gel derived bioactive glass compositions described herein include surgical treatment of periodontal and osteoinfections, inclusion in preparations to cure skin infections, use as a preservative in cosmetic preparations, introduction as antimicrobial agent in health care products and in detergents, and as preventative antimicrobial agents for surgery that involves the use of implanted biomaterials and/or devices.

In addition to the bioactive glass composition, the formulations can include other therapeutic agents such as antibiotics, antivirals, healing promotion agents, anti-inflammatory agents, immunosuppressants, growth factors, anti-metabolites, cell adhesion molecules (CAMs), bone morphogenic proteins (BMPs), vascularizing agents, anticoagulants, and topical anesthetics/analgesics.

The antibiotics can be topical antibiotics suitable for skin treatment. Examples of such antibiotics include but are not limited to: chloramphenicol, chlortetracycline, clyndamycin, clioquinol, erythromycin, framycetin, gramicidin, fusidic acid, gentamicin, mafenide, mupiroicin, neomycin, polymyxin B, bacitracin, silver sulfadiazine, tetracycline and chlortetracycline.

Suitable antivirals include topical antivirals, such as acyclovir, and gancyclovir. Suitable anti-inflammatory agents include corticosteroids, hydrocortisone and nonsteroidal antinflammatory drugs. Suitable growth factors include basic fibroblast growth factor (bFGF), epithelial growth factor (EGF), transforming growth factors $\alpha$ and $\beta$ (TGF $\alpha$ and $\beta$), platelet-derived growth factor (PDGF), and vascular endothelial growth factor/vascular permeability factor (VEGF/VPF)). Suitable topical anesthetics include benzocaine and lidocaine.

In one embodiment, the therapeutic agent is one which would otherwise cause an inflammation at the site at which it is delivered, and the bioactive glass compositions reduce the associated inflammation. For example, a number of compounds, for example, amine compounds, result in inflammation when administered topically, i.e., in a transdermal patch.

In addition, the bioactive glass may be combined with any biocompatible material, such as biodegradable polymer like polylactic/glycolic acid to form a composite material for accelerating wound healing.

The proportion of other therapeutic agents varies according to the agent and the nature of the application. However, the preferred proportions are such that the amount of the agent administered to the patient is in a dosage range accepted within standard medical care.

III. Articles of Manufacture Including Bioactive Glass

The silver-containing, sol-gel derived bioactive glass compositions can be incorporated into implanted materials, such as prosthetic implants, sheets, pins, valves, sutures, stents, screws, plates, tubes, and the like, by incorporating bioactive glass particles into the implanted materials. The compositions can be moldable or machinable.

Table 2, below, shows a relation between the form of the bioactive glass composition and the intended function. This table is not intended to limit the type of form which can be used for an intended function, merely to exemplify types of forms and matching functions. The compositions described herein can be in any of these forms.

TABLE 2

| Form | Function |
| --- | --- |
| Powder | Therapeutic treatment, tissue regeneration, space filling |
| coating | Tissue bonding, thromboresistance, corrosion protection, therapeutic treatment, preventative treatment and tissue ingrowth |
| bulk | Replacement and augmentation of tissue, replace functioning parts |
| fiber | Sutures, electric stimulation |

The articles of manufacture are imparted with anti-bacterial properties via the incorporation of the silver ions into the bioactive glass, which will allow the articles to be implanted, or used to culture cells, with a reduced likelihood of bacteriological contamination.

Cell Growth and Culture

There are many solutions used for culturing cells. These include Dulbecco's minimal essential media, Hank's balanced salt solution, and others. These solutions are essentially isotonic with the cells to be cultured. A problem associated with cell culture is often the growth of bacteria in culture along with the desired cells. Bacterial growth can be minimized by incorporating the bioactive glass compositions into matrices used in cell culture and tissue engineering applications.

V. Methods for Improving Wound Healing

The silver-containing, sol-gel derived bioactive glass fibers, particles and/or coatings are capable of dramatically reducing the amount of time necessary for wound healing to occur. Implants including the fibers, particles or coatings, preferably highly porous fibers or particles, alone or in combination with other anti-bacterial agents, can augment the natural healing process. The effectiveness of the fibers, particles and coatings described herein is most dramatically illustrated in immune compromised patients whose ability to heal wounds is somewhat suppressed.

In one embodiment, the fibers and/or particles are used to fill voids, including voids created during medical procedures. For example, during a root canal operation, the hollowed-out tooth can be filled with a composition including bioactive glass fibers and/or particles. This will help prevent bacterial infection until the tooth is ultimately filled. Also, bioglass-containing compositions can be used to fill the pockets that can develop between the teeth and gums. Compositions including bioactive glass fibers and/or particles can be used to fill voids present in aneurysms, and prevent bacterial growth inside the filled void. Other voids which can be filled include those formed surgically, such as removal of a spleen, ovary, gall bladder, or tumor.

VI. Methods for Grafting Skin

The methods for grafting skin involve applying meshes or fabrics including the silver-containing, sol-gel derived bioactive glass fibers, particles and/or coatings to either the graft site or donor tissue before it is placed in its intended location. Those interested in a detailed description of skin grafting are referred to "Skin Grafts," in *Selected Readings in Plastic Surgery*, Vol. 7, no. 2, P. L. Kelton, MD, Baylor University Medical Center (1992). The graft may also be further treated with a topical carrier prior to placement. The application of bioactive glass to grafts is intended to increase the likelihood that the graft will "take" and incorporate in the host bed. It is intended that the bioactive glass will act as an intermediary bond between the host and graft tissue, suppress the overall inflammatory response which could lead to rejection, as well as accelerate the overall healing process which will lead to a faster and more successful acceptance.

The bioactive glass fibers, particles and/or coatings can be administered locally to a surgical site to minimize post-surgical adhesions. The compositions can optionally be incorporated into a polymeric material which is applied to the surgical site. Alternatively, the bioactive gel-glass can be used as a coating on polymeric materials which is applied to the surgical site. Preferably, the polymeric material is biodegradable. Suitable polymeric materials for this purpose are disclosed, for example, in U.S. Pat. No. 5,410,016 to Hubbell et al., the contents of which are hereby incorporated by reference. Other materials suitable for this purpose, such as Interceed®, agarose and crosslinked alginate, are well known to those of skill in the art.

Biomedical implants are often associated with inflammation at the site of implantation. Incorporation of the bioactive glass fibers described herein, in particular, the highly porous bioactive glass fibers, into the implants, especially on the surface of the implants, can greatly reduce the inflammation associated with the implants. This can be especially useful in suture materials to minimize the inflammation associated with these materials. The anti-bacterial properties of the compositions also allow the sutures to minimize the infection surrounding the suture site.

The present invention will be more clearly understood with reference to the following non-limiting examples.

EXAMPLES

Example 1

Preparation of Silver-Containing Sol-Gel Derived Bioactive Glasses

Silver-doped 58S sol-gel Bioglass® has been prepared by a sol gel method. The textural characteristics of the material (surface area, pore volume, and average pore diameter) were measured by gas-sorption. The antimicrobial action of the silver-doped gel-glass was compared with a control culture with no gel glass. The bioactivity and dissolution behavior in simulated body fluid of the gel-derived specimen has also been monitored.

Materials Preparation

A bioactive gel-glass of the three-component CaO—$P_2O_5$—$SiO_2$ system, namely the 58S, in which 2% (molar) $Ag_2O$ has been introduced by substitution of CaO, has been formed, hereby referred to as 58S7Ag. The numbers refer to the weight percentage of silica and silver oxide. The mix compositions of the material, as well as the non-silver containing counterpart 58S, are listed in Table 3. The 58S7Ag specimen was always handled in the dark, using a safe light, and was stored in a black-box to preserve it in its oxidized state.

TABLE 3

| | Composition of the materials produced in moles and weight | | | | | | | |
|---|---|---|---|---|---|---|---|---|
| material | $SiO_2$ wt. % | $SiO_2$ mol. % | CaO wt. % | CaO mol. % | $P_2O_5$ wt. % | $P_2O_5$ mol. % | $Ag_2O$ wt. % | $Ag_2O$ mol. % |
| 58S | 58 | 60 | 36 | 36 | 6 | 4 | — | |
| SSS7Ag | 58 | 60 | 29 | 34 | 6 | 4 | 7 | 2 |

Hydrolysis and Copolymerization

The following compounds were added to deionized (DI) water obtained from an instant purifier Micromeg Elgostat in sequential order; 2N nitric acid ($HNO_3$), tetraethoxysilane (TEOS) 99% purity, triethoxyphosphate (TEP) 99% purity A.C.S., $Ca(NO_3)_2$—$4H_2O$ 99% purity A.C.S., and $AgNO_3$ 99.99% purity. After two hours of moderated stirring the mixture was poured into polymethylpentane pots, hermetically sealed, and left to gel at room temperature for two days.

Aging

The pots containing the gels were transferred to an oven at 60° C. Aging took three days.

Drying

The aged gels were placed on a watch glass in a drying chamber above 250 ml of DI water. Thus, the near equilibrium drying conditions were realized, in which the pore liquor evaporating from the gel was supported by the vapor pressure of the water.

The drying schedule involves three stages, listed in Table 4. The temperature gradient between each step was 0.1° C./minute.

TABLE 4

Heating program for drying step.

| Stage | Time (hours) | Temperature (° C.) |
|---|---|---|
| 1 | 60 | 20 |
| 2 | 90 | 24 |
| 3 | 130 | 40 |

Stabilization

The stabilization was carried out in a box furnace at 450° C. for 19 hours,

Textural Characterization

Surface Analysis

The textural characterization was performed on a six port Quantachrome AS6 Autosorb and two single port Quantachrome AS I Autosorb gas sorption systems. The instruments determined isotherms volumetrically at 77.4 K. The adsorptive gas was nitrogen, $N_2$, of 99.999% purity. The cross sectional area of adsorbed nitrogen molecules was taken to be 0.162 $nm^2$ for the purposes of specific surface area calculations.

Prior to nitrogen sorption, all samples were degassed under vacuum pressure lower than 1 Pa. at 25° C. for 19 hours to remove physically adsorbed material from their surfaces.

Each isotherm comprised a minimum of 20 adsorption and 20 desorption points measured at equilibrium. At least four adsorption points in the relative pressure range $0.05<P/P_o<0.25$ (where $P_o1$ is the saturated vapor pressure) were used in the calculation of the BET surface area in each case. It was ensured that the slope and intercept of the BET plots were positive and that the product moment correlation coefficients were not less than 0.9999. Two isotherms were collected for each sample to ensure that the data was representative. Data from the second isotherms has been used in the evaluation of the textural parameters reported here. The specific surface areas and pore volumes were estimated in relation to the masses of the samples.

Skeletal Density

The skeletal density (true density) was measured by helium ultrapycnometry using a Quantachrome helium Ultrapycnometer 1000. The instrument uses the ideal gas equation PV=nRT to measure the volume occupied by the sample. The mass of the samples was measured using a four-decimal place digital balance.

The instrument was calibrated immediately before running the analysis. The measurements were repeated 80 times to ensure reproducibility.

Treatment of Data

The most widely employed model for the evaluation of specific surface area is the BET method which is based upon the measurement of quantities of gas physisorbed onto a surface at equilibrium pressure. This method yields reliable results for isotherms of type II and IV (according to Brunauer and IUPAC classifications).

Estimates of specific pore volume were obtained from the amount of nitrogen taken up by the samples in the range $0.9947<P/P_o<0.9956$. Pore size distributions were calculated from desorption data by the BJH method (Barret E. P., Joiner L. G. & Halenda P. P., *J. Am, Chem. Soc.,* 73, 1951, pp. 373–380).

The standard deviations of the means were calculated of-the specific surface area, specific pore volume, mean pore diameter, modal pore diameter, and skeletal density have also been evaluated. The 95% confidence limits were also estimated. It was assumed that the sample population conformed to a Gaussian distribution.

EDAX Analysis

Since the material looked visibly non homogeneous (white, reddish and black shades were observable) three pieces of three different shades of color were selected, coated with carbon and subjected to qualitative and quantitative energy dispersive X-ray analysis (EDAX). The principle behind this technique is the following: an incident electron beam causes atoms to undergo an energy transition to a higher electronic state; the X ray radiation emitted to return to their fundamental electronic state, which is characteristic for each element, is then collected by the instrument.

In Vitro Bioactivity and Dissolution Study

Preparation of Simulated Body Fluid (SBF) Solution

All the chemicals required for this preparation had the highest purity grade available. The reagents were added to 700 ml of DI water, at 36.5° C. under constant stirring, in the following order: 7.996 g of NaCl, 0.35 g of $NaHCO_3$, 0.224 g KCl, 0.228 g of $K_2HPO_4$—$3H_2O$, 0.305 g of $MgCl_2$—$6H_2O$, 40 ml of 1N HCl, 0.368 g of $CaCl_2$, 0.071 g of $Na_2SO_4$, and 0.057 g of $(CH_2OH)_3CNH_2$. The pH was then adjusted with 1N HCl to 7.25, and finally, the solution was made up to 1 liter in a volumetric flask. The solution was stored at 40° C. in polyethylene bottles for no longer than 1 month.

Bioactivity Test

Immersion of powder or bulk samples of bioactive glass in SBF (which resembles the composition of human blood plasma) initiates the surface reactions that lead to the deposition of a bone-like HCA layer. The results are shown in Table 5. The kinetics of HCA formation observed with this in vitro experimental method correlate adequately with the results of in vivo studies.

TABLE 5

Ionic concentrations of the SBF solution and human blood plasma in mmol/CC.

| ion | SBF | human blood plasma |
|---|---|---|
| $Na^+$ | 142 | 142.0 |
| $K^+$ | 5.0 | 5.0 |
| $Mg^{2+}$ | 1.5 | 1.5 |
| $Ca^{2+}$ | 2.5 | 2.5 |
| $Cl^-$ | 147 | 103.0 |
| $HCO_3^-$ | 4.2 | 27.0 |
| $HPO_4^{2-}$ | 1.0 | 1.0 |
| $SO_4^{2-}$ | 0.5 | 0.5 |

58S7Ag specimens (cuboids weighting ~60 mg each) were immersed in 10 ml of SBF in PMP containers, which were sealed and placed in a water bath at 37° C., for different time intervals. Each experiment was carried out in triplicate. The specimens were recovered at the required times and dried in an oven at 60° C. for at least 4 hours. The immersion times varied between 1 hour and 7 days.

The dissolution of the constituents of the gel-glass was studied with quantitative Inductively Coupled Plasma analysis (ICP) which is based on atomic emission spectrometry. The principle of this analytical technique is the following: a solution of the element whose concentration is to be determined, is introduced into the ICP ionizing torch as aqueous aerosol, the light emitted by the atoms or ions is detected by the spectrometer and the concentration is computed by comparison with a standard solution. The release of Si, Ca, P, and Ag ions into the SBF solution was monitored using this technique. The instrument detection limits for the elements of interest were respectively 0.050, 0.100, 0.200, and 0.020 ppm.

The growth of the HCA layer was monitored using a Midac Series FTIR spectrophotometer. The spectra were recorded between 400 and 1600 $cm^{-1}$, measuring the diffuse radiation reflected by the surface of the bulk sample. This is a non destructive analysis which does not require the preparation of a KBr disc.

Antibacterial Tests

58S7Ag was ground to powder with a mortar and pestle and sieved within the particle size range 90–710 μm. The antimicrobial effect of the powder samples was investigated on liquid cultures of *E. coli* (strain MG1655). The growth medium for the bacteria was LB, a rich medium prepared with bacto-tryptone, yeast extract, and NaCl.

A 5 ml starter culture of *E. coli* was incubated for 6 hours. 100 μl of this culture were then inoculated in 5 ml of LB medium containing 100 mg and 200 mg of 58S7Ag. A control sample, containing only the cell inoculum in LB, was also cultured. Each experiment was carried out in triplicate. The cultures were put in an orbital shaker and incubated at 37° C. for 20 hours.

The antibacterial action was estimated from the percentage of growth of *E. Coli*. The concentration of cells in suspension was calculated from optical density measurements of the turbidity of the solutions using a spectrophotometer reading the absorbance at 600 nm. The absorbance values have been "normalized" by subtracting the optical density readings of the non-inoculated LB culture medium.

Statistical Treatment of Data

The measurements of the optical densities of the sample populations (*E. coli*+58S7Ag) were compared with the control culture population using the assumption that their standard deviations were not significantly different. A "pooled" estimate of standard deviation S is calculated using the formula:

$$S^2 \frac{\{(n_1-1)s_1^2 + (n_2-1)s_2^2\}}{(n_1+n_2-2)}$$

Equation 7 where $s_1$ and $s_2$ are the two standard deviations to compare. The value of t (at $n_1+n_2-2$ degrees of freedom) is given by:

$$t = \frac{(\bar{x}_1 - \bar{x}_2)}{S\sqrt{1/n_1 = 1/n_2}}$$

Equation 8

RESULTS

EDAX Analysis

EDAX spectrum were obtained, which confirmed the presence of all the species introduced during the mixing step of the sol-gel process. Peaks observed at 1.760, 2,020, 3.020, as well as two peaks observed around 3.720 keV represent Si, P, Ag, and Ca respectively. Irrespective of the in-homogeneous appearance of the material, quantitative EDAX analysis showed an overall homogeneity of composition of the 58S7Ag (Table 6).

The relative concentrations of network modifiers Ca, P, and Ag are lower than is indicated by the nominal mix composition, due to leaching during gelling and drying.

TABLE 6

Quantitative EDAX analysis on three different pieces of 58S7 Ag.

| Sample | $SiO_2$ % (weight) | CaO % (weight) | $P_2O_5$ % (weight) | $Ag_2O$ % (weight) |
|---|---|---|---|---|
| 1 | 78 | 17 | 3 | 2 |
| 2 | 75 | 19 | 2 | 4 |
| 3 | 75 | 20.5 | 0.5 | 4 |
| Average | 76 | 18.83 | 1.83 | 3.33 |
| Stand. Dev | 1.73 | 1.76 | 1.26 | 1.15 |

Textural Characterization

Adsorption and desorption isotherms for nitrogen were taken of the 58S7Ag samples. The isotherms were representative of those collected for all of the 58S7Ag samples, and were of type IV, indicating that the samples are mesoporous (i.e. they possess pore diameters in the range 20 to 500 A). Hysteresis in the multilayer region of the isotherms, denoted by the deviation in pathway of the adsorption and desorption data, is associated with capillary condensation in the mesopore stricture. The hysteresis loops are of type H1 (formerly type A) which indicates the presence of cylindrical pores of narrow pore size distribution.

The modal pore diameters for 58S7Ag are approximately 169 Å respectively. Hence, the modal pore radii, ~85 Å, are notably smaller than the mean pore radii, 135.6 Å. The difference between the two quantities is believed to arise from a combination of factors: deviation from perfect cylindrical geometry, the volume associated with the junctions of the pores, and the existence of a small number of large pores.

The textural features of 58S7Ag are shown below in Table 7.

TABLE 7

The textural features of 58S7 Ag.

| 58S7 Ag | $Sb_{et}$, Specific surface Area ($m^2/g$) | Vp, Specific pore volume ($cm^3/g$) | Mean pore diameter+ Å | Modal pore diameter+ Å | True density $g/cm^{-3}$ |
|---|---|---|---|---|---|
| Mean value | 76.2 | 0.502 | 271.3 | 169.4 | 2.34 |
| Standard deviation, s | 5.2 | 0.0096 | 21.9 | 14.4 | 0.01 |
| % standard deviation | 6.8% | 1.9% | 8.0% | 8.5% | 0.6% |
| 95% confidence limits | ±13.06 | ±0.024 | ±34.8 | ±22.9 | ±0.011 |

+$2V_p/S_{BET}$

The calculated value of the bulk density of 58S7Ag is 1.0759 $g/cm^{-3}$, which denotes a highly porous silica matrix.

Bioactivity and Dissolution Behavior

FTIR spectra of 58S7Ag as a function of residence time in SBF were taken. The spectra show peaks at 605 and 567 $cm^{-1}$ corresponding to the bending vibrations of the phosphate P—O bonds. The broad peak around 460 $cm^{-1}$ arises from to the bending vibration of amorphous silica and the peak at 1100 $cm^{-1}$ is assigned to the Si—O stretching vibration mode. The bioactivity test in vitro for the 58S7Ag showed a high rate of HCA deposition. The growth of hydroxyapatite is already visible after 3.5 hours and increases with time while silica peaks become less predominant, as shown by the FTIR spectra.

Ionic concentration curves were obtained from ICP analysis, and these curves were consistent with the FTIR results. Each data point plotted was the mean of three measurements. After 48 hours there was a notable decrease in the phosphate concentration, indicating the precipitation of hydroxyapatite. The silicon dissolution rate is still high after the first 3 days. The very slow release of the silver ion into the solution suggests that it is strongly chelated by the silicate network. The maximum silver concentration observed after 7 days was still lower than 30 $\mu$M, which is considered safe from the toxicological stand point.

Antibacterial Properties

The effect of 58S7Ag on *E. coli* MG1655 after 20 hours of incubation was determined. The intensity of absorbance at 600 nm is a measure of optical density, which, in turn, is a measure of the *E. coli* cell-concentration. The results indicate that the presence of 58S7Ag (brown column) greatly inhibited the growth of *E. coli* MCT1655, resulting in a cell concentration 85% lower than the control after 20 hours of incubation. The Ag-doped gel-glass 58S7Ag exhibited a strong antimicrobial response.

ICP data reveal that the release of silicate species from 58S7Ag continues well after the first three days in SBF. The very slow release of silver ions indicates that they are strongly chelated by the silicate network. Rapid dissolution kinetics may be required to obtain an effective antimicrobial action in clinical applications, to prevent the development of antimicrobial resistance. In some embodiments, it may be preferable to prepare silver-doped bioactive gel-glass in which the silver ion is not as strongly bound to the silica matrix. This can be achieved by using a lower stabilization temperature, gel glasses with a larger pore size, a larger volume fraction of pores or a larger concentration of silver dopant.

The percentage composition of the bioactive system $Si_2O$—$CaO$—$P_2O_5$—$Ag_2O$ determined with quantitative EDAX analysis shows that the actual content of network modifiers ($CaO$, $P_2O_5$, $Ag_2O$) in the final product is different from that of the nominal mix composition. This phenomenon may be attributed to the incomplete hydrolysis of TEP and the leaching of soluble ions from the silica network during gelling, washing, and drying.

The sol-gel route has been successfully used to produce a new composition of bioactive gel-glass containing silver oxide. The resulting material is a porous gel-glass having the desired textural characteristics: a mesoporous structure with cylindrically shaped pores which are monomodally dispersed.

An in vitro bioactivity test has shown that the introduction of 3 wt. % silver oxide to the three-component system, $SiO_2$—$CaO$—$P_2O_5$, does not inhibit bioactivity. The dissolution study has confirmed that the material is capable of releasing silicate species (which is very important for its mitogenic effect in vivo) even after the first three days of immersion. The rate of dissolution of silver ions is relevant to eventual clinical applications, since the prerequisite of an effective, topical antimicrobial agent is an immediate and concentrated release of that agent. The dissolution kinetics observed indicated a slow and constant rate of dissolution over a period of seven days. Modification to the sol-gel process may yield a material that can control the release kinetics of silver ions and be tailored for a specific clinical application.

What is claimed is:

1. A composition comprising silver-containing sol-gel derived bioactive glass wherein the bioactive glass is an inorganic glass material having an oxide of silicon as its major component and which bonds with growing tissue when reacted with physiological fluid.

2. The composition of claim 1, in the form of particles, fibers or coatings.

3. The composition of claim 1, further comprising one or more therapeutic agents.

4. The composition of claim 3, wherein therapeutic agent(s) are selected from the group consisting of healing promotion agents, growth factors, anti-inflammatory agents and topical anesthetics.

5. The composition of claim 3, wherein the therapeutic agent is a topical antibiotic.

6. The composition of claim 5, wherein the topical antibiotic is selected from the group consisting of chloramphenicol, chlortetracycline, clyndamycin, clioquinol, erythromycin, framycetin, gramicidin, fusidic acid, gentamicin, mafenide, mupiroicin, neomycin, polymyxin B, bacitracin, silver sulfadiazine, tetracycline, chlortetracycline and combinations thereof.

7. The composition of claim 1, wherein the bioactive glass has a porosity between 10 and 80 percent.

8. The composition of claim 1, wherein the bioactive glass has the following composition by weight percentage:

| Component | Percent |
|---|---|
| $SiO_2$ | 45–86 |
| CaO | 6–50 |
| $P_2O_5$ | 0–12 |
| $Ag_2O$ | 0.1–12 |
| $Al_2O_3$ | 0–3 |
| $CaF_2$ | 0–25 |
| $B_2O_3$ | 0–20 |
| $K_2O$ | 0–8 |
| MgO | 0–5 |
| $Na_2O$ | 0–20. |

9. The composition of claim 1, wherein the bioactive glass has the following composition by weight percentage:

| Component | Percent |
|---|---|
| $SiO_2$ | 45–86 |
| CaO | 10–36 |
| $P_2O_5$ | 3–12 |
| $Ag_2O$ | 3–12 |
| $CaF_2$ | 0–25 |
| $B_2O_3$ | 0–10 |
| $K_2O$ | 0–8 |
| MgO | 0–5. |

10. The composition of claim 2, wherein the particles, fibers or coatings have a pore size in the range of between about 20–400 angstroms.

11. The composition of claim 2, wherein the particles, fibers or coatings have a surface area in the range of between about 20–400 $m^2/g$.

12. A method for treating wounds and burns comprising contacting a wound with an effective wound healing amount of the composition of claim 1.

13. A method for grafting skin comprising applying the composition of claim 1 to a graft site, the donor tissue, or both.

14. The method of claim 13, further comprising the application of a topical antibiotic to the graft site, the donor tissue, or both.

15. A wound or burn dressing comprising a bandage comprising the particles, fibers or coatings of claim 2 and a topical antibiotic.

16. The composition of claim 1, wherein the composition has been combined with a biocompatible, biodegradable material to form a composite material.

17. The composition of claim 1, wherein the composition is part of a matrix used for tissue engineering.

18. The composition of claim 2, wherein the composition is in the form of fibers.

19. The composition of claim 18, wherein the composition is incorporated into a bone graft substitute.

20. The composition of claim 1, wherein the composition is incorporated into an implantable material.

21. The composition of claim 20, wherein the implantable material is selected from the group consisting of prosthetic implants, sheets, pins, valves, sutures, stents, screws, plates, and tubes.

* * * * *